US011134982B2

(12) United States Patent
Suzuki et al.

(10) Patent No.: US 11,134,982 B2
(45) Date of Patent: Oct. 5, 2021

(54) MEDICAL ELONGATED BODY AND MEDICAL INSTRUMENT SET

(71) Applicant: TERUMO KABUSHIKI KAISHA, Tokyo (JP)

(72) Inventors: Kenta Suzuki, Fujinomiya (JP); Kota Hamuro, Fujinomiya (JP); Takito Inukai, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 153 days.

(21) Appl. No.: 16/583,411

(22) Filed: Sep. 26, 2019

(65) Prior Publication Data

US 2020/0038056 A1 Feb. 6, 2020

Related U.S. Application Data

(63) Continuation of application No. PCT/JP2018/012430, filed on Mar. 27, 2018.

(30) Foreign Application Priority Data

Mar. 31, 2017 (JP) .............................. JP2017-071981

(51) Int. Cl.
*A61B 17/34* (2006.01)
*A61B 17/00* (2006.01)
(Continued)

(52) U.S. Cl.
CPC ...................... *A61B 17/3423* (2013.01); *A61B 2017/00292* (2013.01); *A61B 2017/00778* (2013.01);
(Continued)

(58) Field of Classification Search
CPC ........ A61B 17/3423; A61B 2017/3425; A61B 2017/00778; A61B 2017/00292;
(Continued)

(56) References Cited

U.S. PATENT DOCUMENTS 4,564,014 A 1/1986 Fogarty et al.
4,616,652 A 10/1986 Simpson
(Continued)

FOREIGN PATENT DOCUMENTS

JP 2000116787 A 4/2000
JP 2000300510 A 10/2000
(Continued)

OTHER PUBLICATIONS

International Search Report (PCT/ISA/210) and translation and Written Opinion (PCT/ISA/237) dated Jun. 19, 2018, by the Japanese Patent Office as the International Searching Authority for International Application No. PCT/JP2018/012430.

*Primary Examiner* — Richard G Louis
(74) *Attorney, Agent, or Firm* — Buchanan Ingersoll & Rooney PC

(57) ABSTRACT

A rapid exchange type medical elongated body is disclosed in which an outer diameter of a distal portion of a tubular member is set smaller than an outer diameter of a proximal portion of the tubular member, which prevents an occurrence of a kink in a physical property change region of the medical elongated body which has a relatively large change in physical property. A tubular member forming a second region of a distal member of a medical elongated body is integrally formed with a shaft portion. The distal member has a reinforcement layer containing a metallic material and formed between an inner layer and an outer layer from a first region to the second region. The reinforcement layer is disposed inside the tubular member in the second region. An outer diameter of the first region is set smaller than an outer diameter of the second region.

16 Claims, 7 Drawing Sheets

(51) Int. Cl.
*A61M 25/00* (2006.01)
*A61M 25/01* (2006.01)

(52) U.S. Cl.
CPC .. *A61B 2017/3425* (2013.01); *A61M 25/0068* (2013.01); *A61M 25/0108* (2013.01)

(58) Field of Classification Search
CPC .......... A61M 25/01; A61M 2025/0059; A61M 2025/0183; A61M 2025/0681; A61M 25/0662; A61M 25/005; A61M 25/0108; A61M 25/0068; A61M 31/005; A61M 25/0097

See application file for complete search history.

(56) References Cited

U.S. PATENT DOCUMENTS

| | | |
|---|---|---|
| 4,762,129 A | 8/1988 | Bonzel |
| 4,813,930 A | 3/1989 | Elliott |
| 4,832,028 A | 5/1989 | Patel |
| 4,932,413 A | 6/1990 | Shockey et al. |
| 5,098,412 A | 3/1992 | Shiu |
| 5,120,323 A | 6/1992 | Shockey et al. |
| 5,122,125 A | 6/1992 | Deuss |
| 5,232,445 A | 8/1993 | Bonzel |
| 5,267,982 A | 12/1993 | Sylvanowicz |
| 5,385,562 A | 1/1995 | Adams et al. |
| 5,441,489 A | 8/1995 | Utsumi et al. |
| 5,472,425 A | 12/1995 | Teirstein |
| 5,527,292 A | 6/1996 | Adams et al. |
| 5,658,263 A | 8/1997 | Dang et al. |
| 5,776,141 A | 7/1998 | Klein et al. |
| 6,066,126 A | 5/2000 | Li et al. |
| 6,159,195 A | 12/2000 | Ha et al. |
| 6,338,725 B1 | 1/2002 | Hermann et al. |
| 6,475,195 B1 | 11/2002 | Voda |
| 6,575,958 B1 | 6/2003 | Happ et al. |
| 6,595,952 B2 | 7/2003 | Forsberg |
| 6,610,068 B1 | 8/2003 | Yang |
| 6,638,268 B2 | 10/2003 | Niazi |
| 6,689,144 B2 | 2/2004 | Gerberding |
| 6,695,793 B2 | 2/2004 | Bemnan et al. |
| 6,706,018 B2 | 3/2004 | Westlund et al. |
| 6,755,812 B2 | 6/2004 | Peterson et al. |
| 6,860,876 B2 | 3/2005 | Chen |
| 6,866,655 B2 | 3/2005 | Hackett |
| 6,953,454 B2 | 10/2005 | Peterson et al. |
| 7,294,124 B2 | 11/2007 | Eidenschink |
| 7,316,678 B2 | 1/2008 | Nash et al. |
| 7,697,996 B2 | 4/2010 | Manning et al. |
| 7,717,899 B2 | 5/2010 | Bowe et al. |
| 7,762,984 B2 | 7/2010 | Kumoyama et al. |
| 8,048,032 B2 | 11/2011 | Root et al. |
| 8,142,413 B2 | 3/2012 | Root et al. |
| 8,292,850 B2 | 10/2012 | Root et al. |
| 9,352,123 B2 | 5/2016 | Zhou et al. |
| 2003/0195546 A1 | 10/2003 | Solar et al. |
| 2003/0199849 A1 | 10/2003 | Hackett |
| 2004/0116832 A1 | 6/2004 | Friedrich et al. |
| 2004/0127927 A1 | 7/2004 | Adams |
| 2004/0236215 A1* | 11/2004 | Mihara ............. A61M 25/0102 600/434 |
| 2005/0004523 A1 | 1/2005 | Osborne et al. |
| 2005/0182437 A1 | 8/2005 | Bonnette et al. |
| 2005/0234427 A1 | 10/2005 | Eder |
| 2005/0288628 A1* | 12/2005 | Jordan ............. A61M 25/0053 604/96.01 |
| 2007/0239251 A1* | 10/2007 | Prabhu .................... A61F 2/915 623/1.2 |
| 2007/0260219 A1 | 11/2007 | Root et al. |
| 2008/0125752 A1 | 5/2008 | Gunderson et al. |
| 2008/0188832 A1* | 8/2008 | Tanioka ............ A61M 25/0054 604/525 |
| 2009/0177120 A1 | 7/2009 | Tockman et al. |
| 2010/0217237 A1 | 8/2010 | Itou et al. |
| 2010/0324482 A1 | 12/2010 | Farnholtz |
| 2011/0082443 A1 | 4/2011 | Griffin et al. |
| 2018/0344971 A1 | 12/2018 | Suzuki et al. |

FOREIGN PATENT DOCUMENTS

| | | |
|---|---|---|
| JP | 2008110132 A | 5/2008 |
| JP | 2008142351 A | 6/2008 |
| JP | 2008188304 A | 8/2008 |
| JP | 2010131325 A | 6/2010 |
| JP | 2011135989 A | 7/2011 |
| JP | 2012249811 A | 12/2012 |

* cited by examiner

MEDICAL ELONGATED BODY AND MEDICAL INSTRUMENT SET

CROSS-REFERENCES TO RELATED APPLICATIONS

This application is a continuation of International Application No. PCT/JP2018/012430 filed on Mar. 27, 2018, which claims priority to Japanese Application No. 2017-071981 filed on Mar. 31, 2017, the entire content of both of which is incorporated herein by reference.

TECHNICAL FIELD

The present disclosure relates to a medical elongated body and a medical instrument set.

BACKGROUND ART

When performing various procedures on a body lumen such as blood vessel, an operator delivers a guiding catheter (parent catheter) to a location close to a lesion area, for example, to an entrance portion of a coronary artery along a guide wire which has been inserted into the blood vessel in advance. After having guided a distal portion of the guiding catheter to the location close to the lesion area, for example, to the entrance portion of the coronary artery, the operator enables a treatment device such as balloon catheter to advance from the distal portion of the guiding catheter, and performs a procedure on the lesion area (for example, a stenosed site formed in the blood vessel).

For example, when the operator performs a procedure on the stenosed site formed in the coronary artery, if the stenosed site is spaced apart from the entrance of the coronary artery, since the treatment device receives various resistance due to influences of intravascular stenosis or the tortuousness of the blood vessel, it becomes relatively difficult for the operator to insert the treatment device to the lesion area. In this case, after having disposed the guiding catheter at a predetermined location inside the blood vessel, the operator inserts a medical elongated body (child catheter) into the guiding catheter, and delivers the medical elongated body to a position as close to the lesion area as possible. The operator is capable of relatively easily inserting the treatment device into the lesion area by supporting the delivery of the treatment device with the medical elongated body.

As an example of the medical elongated body described above, JP-A-2011-135989 discloses a rapid exchange type (monorail type) catheter including a tubular member (i.e., insertion tube) formed with a lumen into which a treatment device can be inserted, and a linear body (wire) provided on a proximal side of the tubular member.

The medical elongated body described in JP-A-2011-135989 has a covering tube overlapping an outer circumferential surface of a proximal portion of the tubular member, and a hook-shaped interlock portion formed by bending a distal portion of the linear body into a U shape. The hook-shaped interlock portion included in the linear body is connected to the tubular member via the covering tube in a state where the hook-shaped interlock portion is inserted into the lumen of the tubular member.

In the rapid exchange type medical elongated body described in JP-A-2011-135989, the lumen is formed only in a tubular body disposed on a distal side, and thus the operator is capable of saving the time and effort taken to insert the treatment device over the entire length of the medical elongated body, and easily inserting the treatment device into the medical elongated body. In addition, the medical elongated body described in JP-A-2011-135989 has a small area of contact between a guiding catheter which is a parent catheter and the linear body of the medical elongated body. For this reason, the operator is capable of rather smoothly moving the medical elongated body along a lumen of the guiding catheter.

However, when the rapid exchange type medical elongated body described in JP-A-2011-135989 is used to support the delivery of the treatment device, problems can occur.

For example, since the tubular member and the linear body are separate members, the medical elongated body has a relatively large physical property difference in a connection section between the tubular member and the linear body. For this reason, when the medical elongated body is delivered to the vicinity of a lesion area, the medical elongated body has a potential for kinking in the connection section between the tubular member and the linear body.

In addition, in the rapid exchange type medical elongated body, it is necessary to prevent a proximal opening portion, which is provided on the proximal side of the tubular member, from moving to a distal side of the guiding catheter in the middle of a procedure using the medical elongated body. For this reason, in the middle of the procedure, it is necessary for the operator to figure out the position of the proximal side of the tubular member. However, in the medical elongated body, if a contrast marker (contrast ring) typically used in a catheter device is disposed in the proximal portion of the tubular member, the influence of the rigidity of the contrast marker increases a physical property difference in the vicinity of a boundary portion between the tubular member and the linear body. Therefore, the medical elongated body is likely to kink.

Note that in the medical elongated body described in JP-A-2011-135989, as described above, the hook-shaped interlock portion formed in the distal portion of the linear body overlaps the outer circumferential surface of the proximal portion of the tubular member. For this reason, if the linear body and the tubular member are formed of a metallic material, in the medical elongated body, there can be a partial improvement in the contrast property of the vicinity of the proximal portion of the tubular member. Since the range of a portion of the medical elongated body which has an improved contrast property is limited corresponding to an exterior shape (hook shape) of the linear body, it can be difficult to improve the contrast property of the vicinity of the proximal portion of the tubular member to a desired level.

In addition, in the medical elongated body, the outer diameter of the distal portion of the tubular member is preferably set smaller than the outer diameter of the proximal portion of the tubular member. Since the medical elongated body is formed as described above, the distal portion of the tubular member can be delivered relatively smoothly to the lesion area.

SUMMARY OF DISCLOSURE

A rapid exchange type medical elongated body is disclosed in which an outer diameter of a distal portion of a tubular member is smaller than an outer diameter of a proximal portion of the tubular member, which can help prevent an occurrence of a kink in a physical property change region of the medical elongated body which has a relatively large change in physical property, and in which a contrast property of the vicinity of the proximal portion of the tubular member can be improved, and a medical instrument set including the medical elongated body and a catheter.

According to an embodiment of the present disclosure, a medical elongated body is disclosed, which includes a shaft portion made of a linear body; and a distal member formed on a distal side of the shaft portion and having a lumen, in which the distal member has a first region having an inner layer and an outer layer which are made of a resin material, and a second region having the inner layer, the outer layer, and a tubular member made of a metallic material and disposed between the inner layer and the outer layer, in which the tubular member forming the second region is integrally formed with the shaft portion, in which the distal member has a reinforcement layer containing a metallic material and formed between the inner layer and the outer layer from the first region to the second region, in which the reinforcement layer is disposed inside the tubular member in the second region, and in which an outer diameter of the first region is set smaller than an outer diameter of the second region.

In the medical elongated body with the foregoing configuration, the shaft portion made of a linear body is integrally formed with the tubular member forming the second region of the distal member. For this reason, in the medical elongated body, a physical property difference can be kept small at a boundary portion (physical property change region) between the shaft portion and the tubular member, and the occurrence of a kink can be prevented at the boundary portion.

In addition, the medical elongated body with the foregoing configuration is capable of improving the contrast property of the second region by virtue of the tubular member forming the second region, and the reinforcement layer containing a metallic material and disposed inside the tubular member in the second region. Therefore, it is not necessary to separately provide a contrast marker (contrast ring) for indicating a proximal side of the second region, and thus the medical elongated body is capable of improving the contrast property of the second region, and preventing an occurrence of a physical property difference resulting from the placement of the contrast marker.

In addition, since the outer diameter of the first region of the distal member is smaller than the outer diameter of the second region, the ease to insert the medical elongated body with the foregoing configuration into a body lumen can be improved.

In accordance with another aspect, a medical elongated body is disclosed comprising: a shaft portion; a distal member formed on a distal side of the shaft portion and having a lumen, the distal member having a first region, a second region, and a third region, the first region having an inner layer and an outer layer, the second region having the inner layer, the outer layer, and a tubular member, the tubular member being disposed between the inner layer and the outer layer in the second region, and an outer diameter of the first region being smaller than an outer diameter of the second region; a reinforcement layer containing a metallic material arranged between the inner layer and the outer layer from the first region to the second region of the distal member, the reinforcement layer being disposed inside of the tubular member in the second region; and the tubular member having an inclined region inclined toward the shaft portion in the third region, the third region including a proximal opening portion and the third region has an outer diameter increasing from a distal side toward a proximal side of the inclined region.

In accordance with an aspect, a medical instrument set is disclosed comprising: a medical elongated body which includes a shaft portion made of a linear body, a distal member formed on a distal side of the shaft portion and having a lumen, the distal member having a first region having an inner layer and an outer layer which are made of a resin material, and a second region having the inner layer, the outer layer, and a tubular member made of a metallic material and disposed between the inner layer and the outer layer in the second region, the tubular member forming the second region being integrally formed with the shaft portion, a reinforcement layer containing a metallic material arranged between the inner layer and the outer layer from the first region to the second region of the distal member, the reinforcement layer being disposed inside of the tubular member in the second region, and wherein an outer diameter of the first region is smaller than an outer diameter of the second region; and a catheter having a catheter main body portion with a lumen into which the medical elongated body is insertable, and wherein a maximum outer diameter of the proximal opening portion of the medical elongated body is equal to or greater than an inner diameter of the catheter main body portion.

DESCRIPTION OF EMBODIMENTS

Set forth below with reference to the accompanying drawings is a detailed description of embodiments of a medical elongated body and a medical instrument set representing examples of the inventive medical elongated body and medical instrument disclosed here. The dimensions or scales on the drawings may be exaggerated or different from actuality/reality for convenience of description and illustration.

Medical Instrument Set

Figure 1:
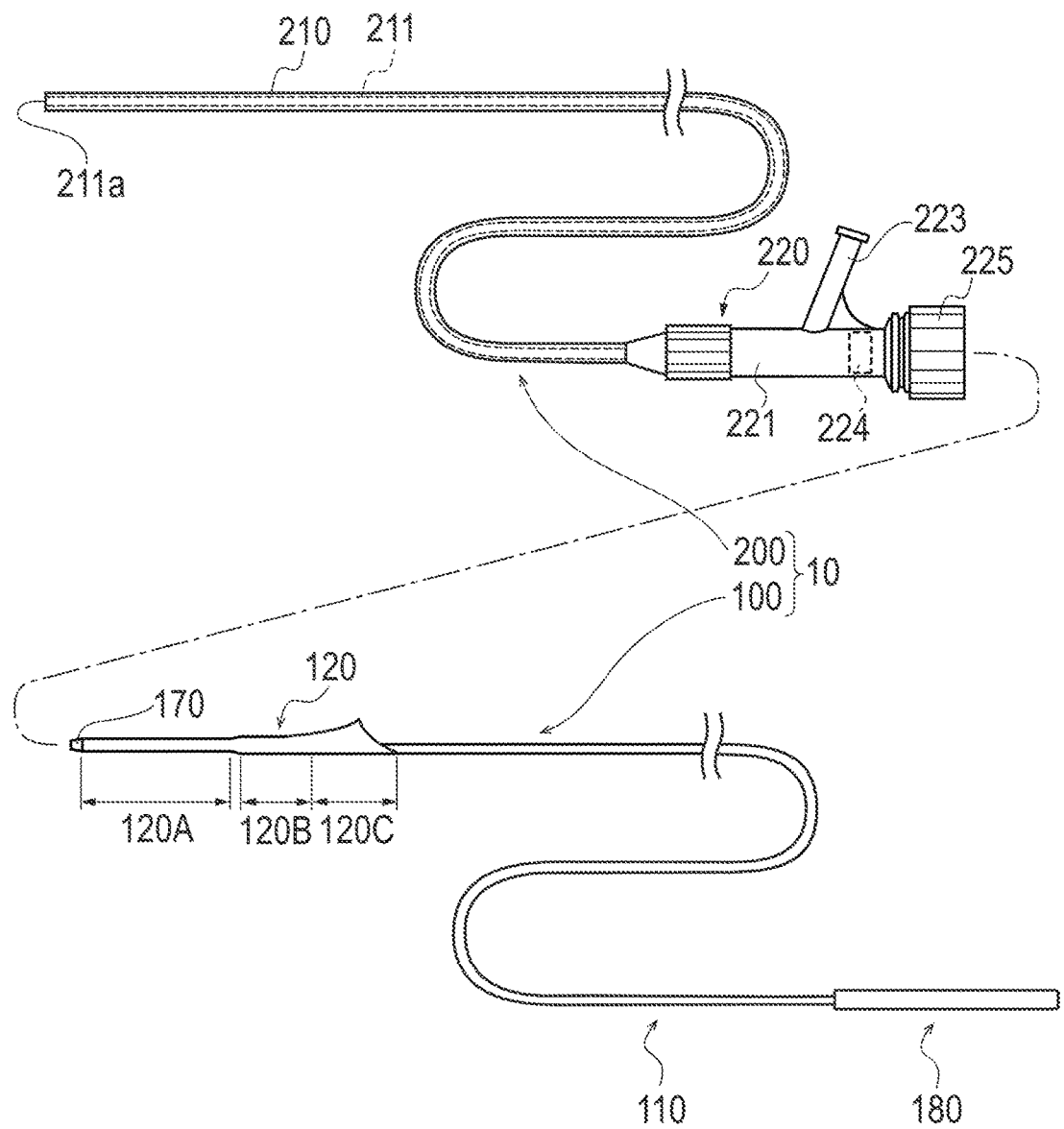
FIG. 1 is a simplified view illustrating a medical instrument set according to an embodiment of the present disclosure.

FIG. 1 illustrates a medical instrument set (catheter set) 10 according to the embodiment.

As illustrated in FIG. 1, the medical instrument set 10 has a medical elongated body 100 and a catheter 200.

In accordance with an exemplary embodiment, the catheter 200 can be configured as a so-called guiding catheter that delivers a medical device (for example, a treatment device such as balloon catheter or stent delivery device, or a diagnosis device such as intravascular ultrasound diagnosis catheter or intravascular optical diagnosis catheter) to a lesion area such as stenosed site when a body lumen such as blood vessel is treated or diagnosed. Generally, the catheter 200 can also be referred to as a parent catheter.

In accordance with an exemplary embodiment, the medical elongated body 100 can be configured as a so-called support catheter that is used for a procedure such as inserting the medical device, which has been delivered to the vicinity of the lesion area such as stenosed site by the catheter 200, into the lesion area, or such as causing the medical device to pass through the lesion area. Generally, the medical elongated body 100 is also referred to as a child catheter.

Catheter

As illustrated in FIG. 1, the catheter 200 has a catheter main body portion 210 formed with a lumen 211 into which a guide wire, the medical device, the medical elongated body 100, or the like can be inserted, and a hub 220 disposed in a proximal portion of the catheter main body portion 210.

In accordance with an exemplary embodiment, the catheter main body portion 210 can be a hollow tubular member having relative flexibility. A distal opening portion 211a is formed at a distal end of the catheter main body portion 210, and communicates with the lumen 211 of the catheter main body portion 210. The catheter main body portion 210 can be formed of (i.e., made of), for example, a resin material.

In accordance with an exemplary embodiment, the hub 220 of the catheter 200 has a Luer tapered connector (Y-connector) 221 that is known in the medical field. The connector 221 has a side branch 223 connected to a tubular member through which a contrast agent or a priming liquid can flow; a valve body 224 disposed inside the hub 220; and an opener 225 for opening and closing the valve body 224. In addition, a proximal port (not illustrated) configured to receive a shaft portion 110 or a distal member 120 of the medical elongated body 100 into and out from the hub 220 can be provided on a proximal side of the hub 220.

When performing a procedure using the medical elongated body 100, an operator inserts a distal side (the shaft portion 110 and the distal member 120) of the medical elongated body 100 into the hub 220 and the catheter main body portion 210 via the proximal port provided in the hub 220 of the catheter 200. If the operator supplies the contrast agent from the side branch 223 in a state where the distal side of the medical elongated body 100 is inserted into the catheter main body portion 210 of the catheter 200, the contrast agent can be discharged to a distal side of the catheter main body portion 210. At that time, the operator is capable of preventing the contrast agent from flowing out from the proximal port of the hub 220 by performing a closing operation of the valve body 224 of the hub 220.

Medical Elongated Body

Figure 2:
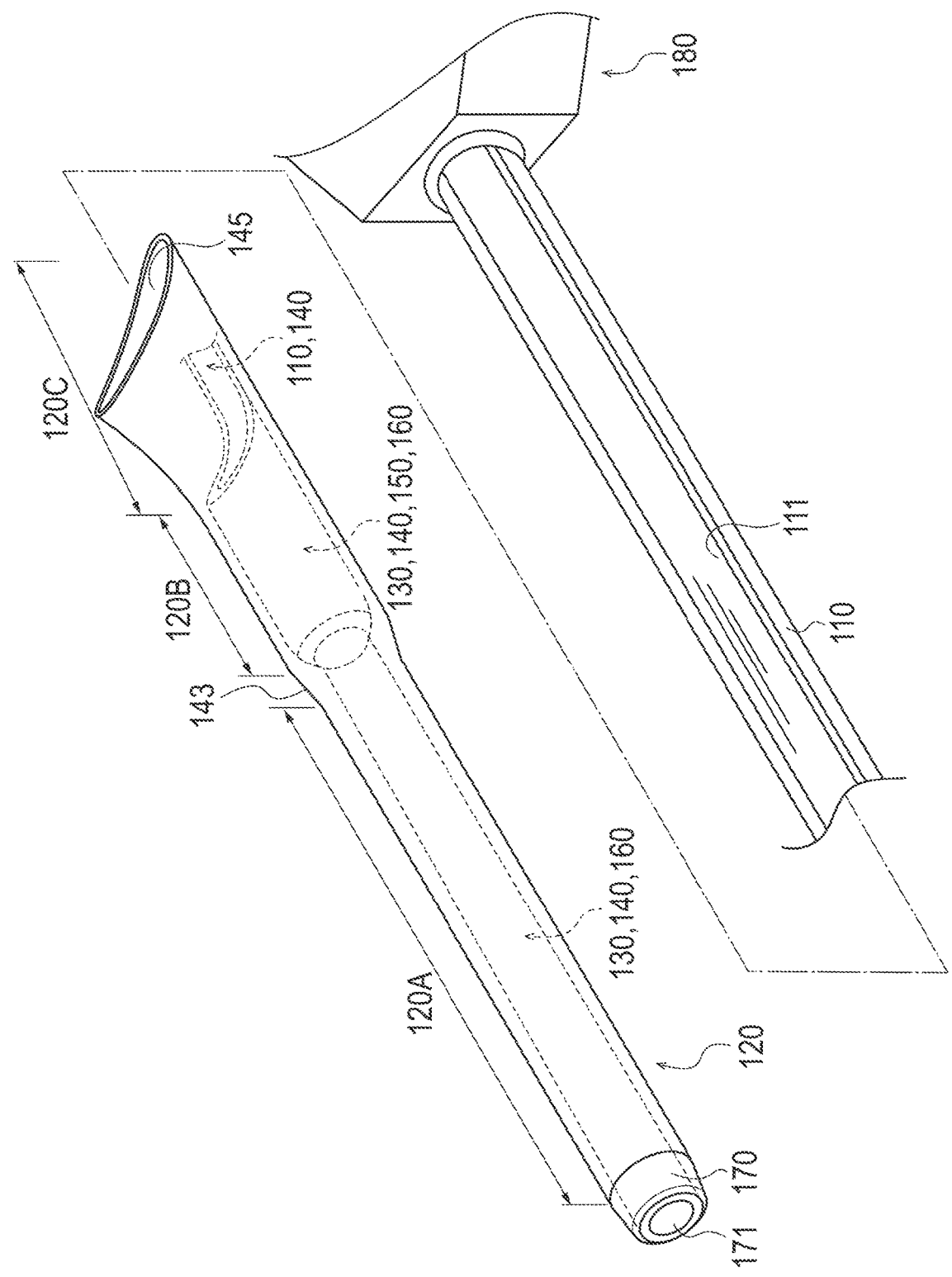
FIG. 2 is a perspective view of a medical elongated body according to the embodiment.

As illustrated in FIGS. 1 and 2, the medical elongated body 100 has the shaft portion 110 made of a linear body; the distal member 120 formed on a distal side of the shaft portion 110; and a grip portion 180 which is disposed on a proximal side of the shaft portion 110 and can be gripped by the fingers of the operator.

As illustrated in FIGS. 1 and 2, the distal member 120 has a first region 120A, a second region 120B, and a third region 120C which are disposed in sequence from a distal side to a proximal side. Note that in FIG. 2, the member number of the main member forming the regions is assigned to each of the regions 120A, 120B, and 120C in order to schematically describe the structure of the distal member 120.

Figure 3:
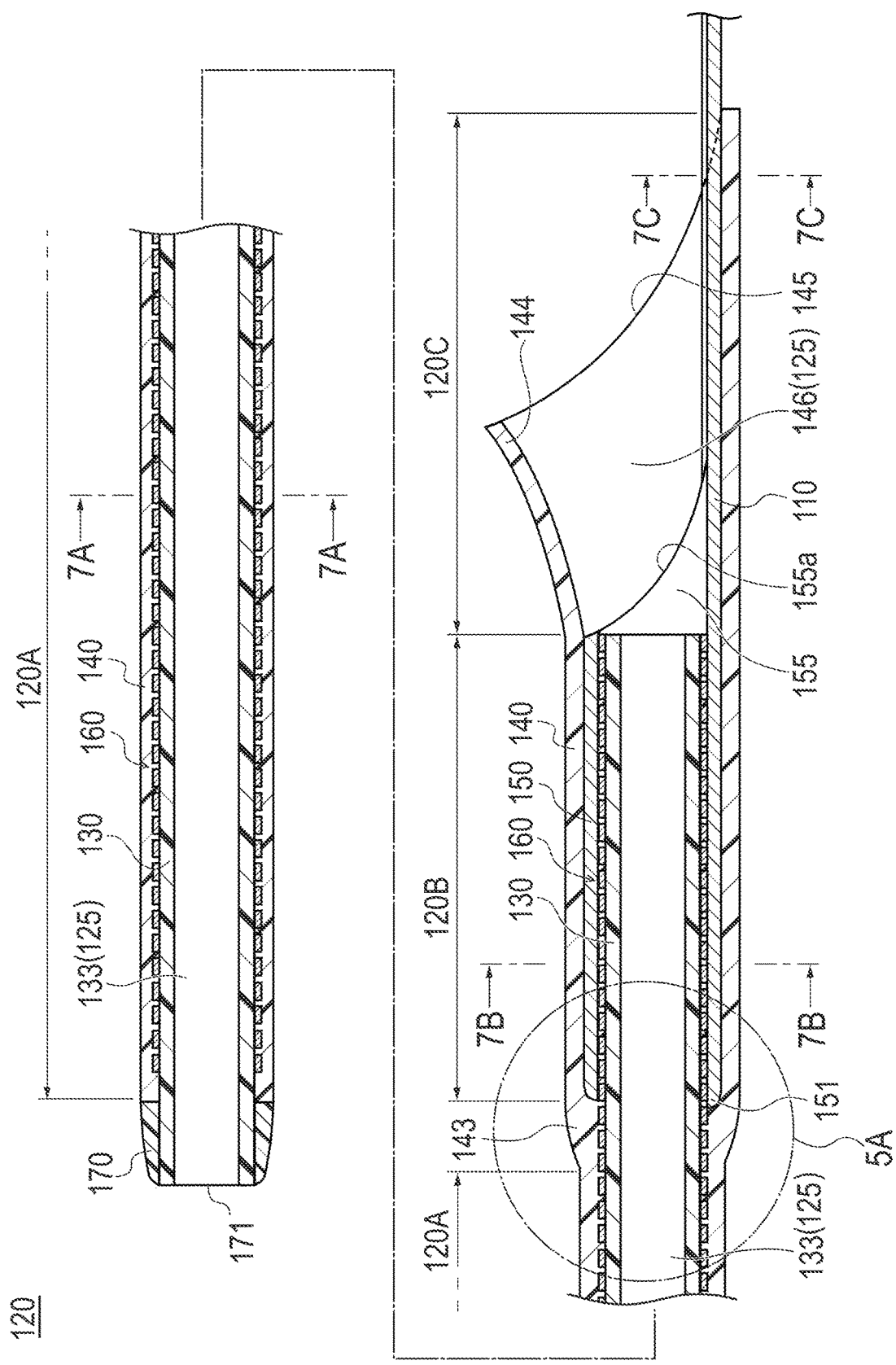
FIG. 3 is an enlarged cross-sectional view of a distal member of the medical elongated body along an axial direction.
Figure 7A:
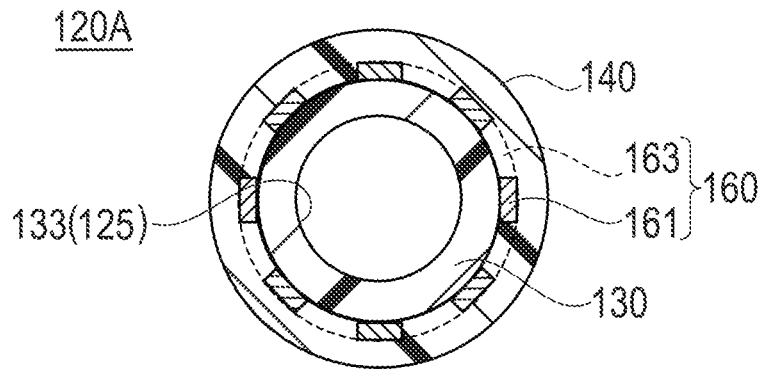
FIG. 7A is an axially orthogonal cross-sectional view of a first region of the distal member taken along an arrow-head line 7A-7A of FIG. 3.

As illustrated in FIGS. 3 and 7A, the first region 120A of the distal member 120 has an inner layer 130 made of a resin material, and an outer layer 140 made of a resin material.

Each of the inner layer 130 and the outer layer 140 is formed as a hollow tubular member extending in an axial direction (right and left direction in FIG. 3) of the distal member 120.

As illustrated in FIG. 3, the inner layer 130 has a lumen 133 formed inside of the inner layer 130. The lumen 133 of the inner layer 130 communicates with a lumen 146 of a proximal portion (a portion of the outer layer 140, which is disposed in the third region 120C) 144 of the outer layer 140. The lumen 133 of the inner layer 130 and the lumen 146 of the proximal portion 144 of the outer layer 140 form a lumen 125 through which the guide wire, the medical device, or the like is inserted into the distal member 120.

As illustrated in FIG. 3, a distal tip 170 is provided on the distal side of the distal member 120, and helps prevent a distal end of the medical elongated body 100 from causing damages to a body organ when the distal end comes into contact with a body lumen (intravascular wall or the like).

The distal tip 170 has a distal opening portion 171 opening at a distal end of the distal tip 170. In addition, the distal tip 170 is fixed (for example, welded) to the inner layer 130 in a state where the distal tip 170 covers a portion of the inner layer 130, which is not covered with the outer layer 140.

Figure 5:
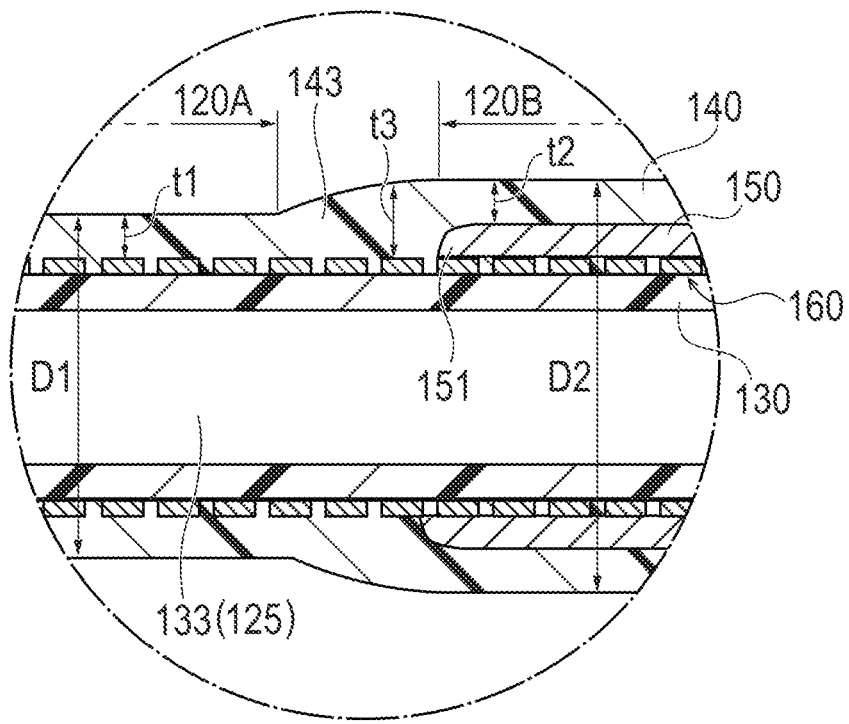
FIG. 5 is an enlarged view illustrating a portion surrounded by a broken line 5A of FIG. 3.

As illustrated in FIG. 5, the outer layer 140 of the distal member 120 can have an inclined portion 143 having an outer diameter decreasing from a distal end of the second region 120B toward the distal side. In accordance with an exemplary embodiment, the inclined portion 143 has a cross-sectional shape that is curved (i.e., gently curved) from a proximal side to the distal side.

The outer diameter (an outer diameter D1 in the first region 120A) of the outer layer 140 in the first region 120A can be, for example, from 1.4 mm to 1.8 mm. In addition, the outer diameter (an outer diameter D2 in the second region 120B) of the outer layer 140 in the second region 120B can be, for example, from 1.7 mm to 2.1 mm.

As illustrated in FIG. 5, in an axially orthogonal cross section of the distal member 120, a wall thickness t1 of the outer layer 140 in the first region 120A closer to the distal side than the inclined portion 143 is substantially the same as a wall thickness t2 of the outer layer 140 in the second region 120B. Note that the range of substantially the same dimension contains, for example, a dimensional difference induced by manufacturing tolerances.

In accordance with an exemplary embodiment, a maximum wall thickness t3 of the inclined portion 143 can be greater than the wall thickness t1 in the first region 120A and the wall thickness t2 in the second region 120B. Transition in the wall thickness of the inclined portion 143 is made such that the wall thickness becomes maximum (i.e., greatest wall thickness) in the vicinity of the distal end of the second region 120B and becomes minimum (i.e., least wall thickness) in the vicinity of a proximal end of the first region 120A.

In accordance with an exemplary embodiment, the outer layer 140 can be formed, for example, by joining together a resin tube (i.e., a tubular member formed from a resin) forming the first region 120A and a resin tube forming the second region 120B. In this case, for example, the tubes (i.e., tubular members) can be welded together by applying heat to the tubes in a state where the resin tube forming the first region 120A is covered with the resin tube forming the second region 120B. In addition, at that time, the wall thickness of an overlapping portion of both tubes (i.e., tubular members) increases by the difference in outer diameter between both tubular members. In accordance with an exemplary embodiment, the first region 120A, the inclined portion 143, and the second region 120B can be integrally formed, each of which includes a predetermined wall thickness, by adjusting the portion with an increased wall thickness such that the outer diameter of the portion decreases to the distal side as illustrated in FIG. 5.

The wall thickness t1 of the first region 120A can be, for example, from 0.04 mm to 0.25 mm. In addition, the wall thickness t2 of the second region 120B can be, for example, from 0.10 mm to 0.30 mm. In addition, the maximum wall thickness t3 of the inclined portion 143 can be, for example, from 0.04 mm to 0.40 mm.

Figure 7B:
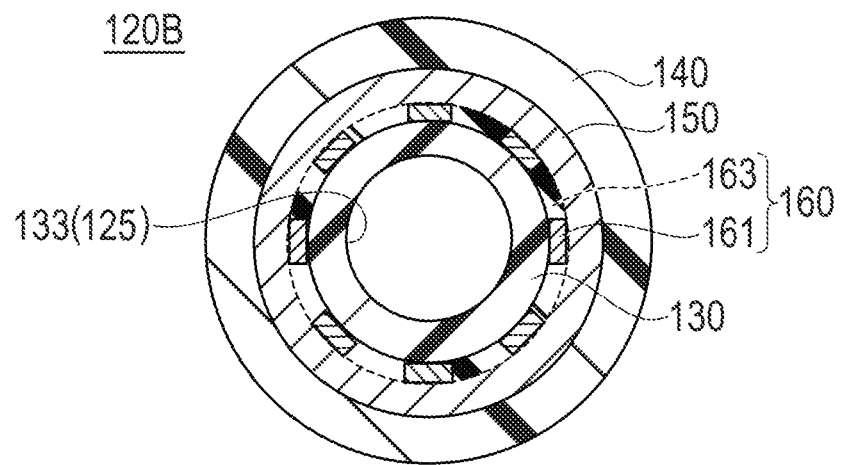
FIG. 7B is an axially orthogonal cross-sectional view of the second region of the distal member taken along an arrow-head line 7B-7B of FIG. 3.

As illustrated in FIGS. 3 and 7B, the second region 120B of the distal member 120 has the inner layer 130; the outer layer 140; and a tubular member 150 made of a metallic material and disposed between the inner layer 130 and the outer layer 140.

In accordance with an exemplary embodiment, the tubular member 150 forming the second region 120B can be integrally formed with the shaft portion 110 extending to a proximal side of the tubular member 150.

Figure 4:
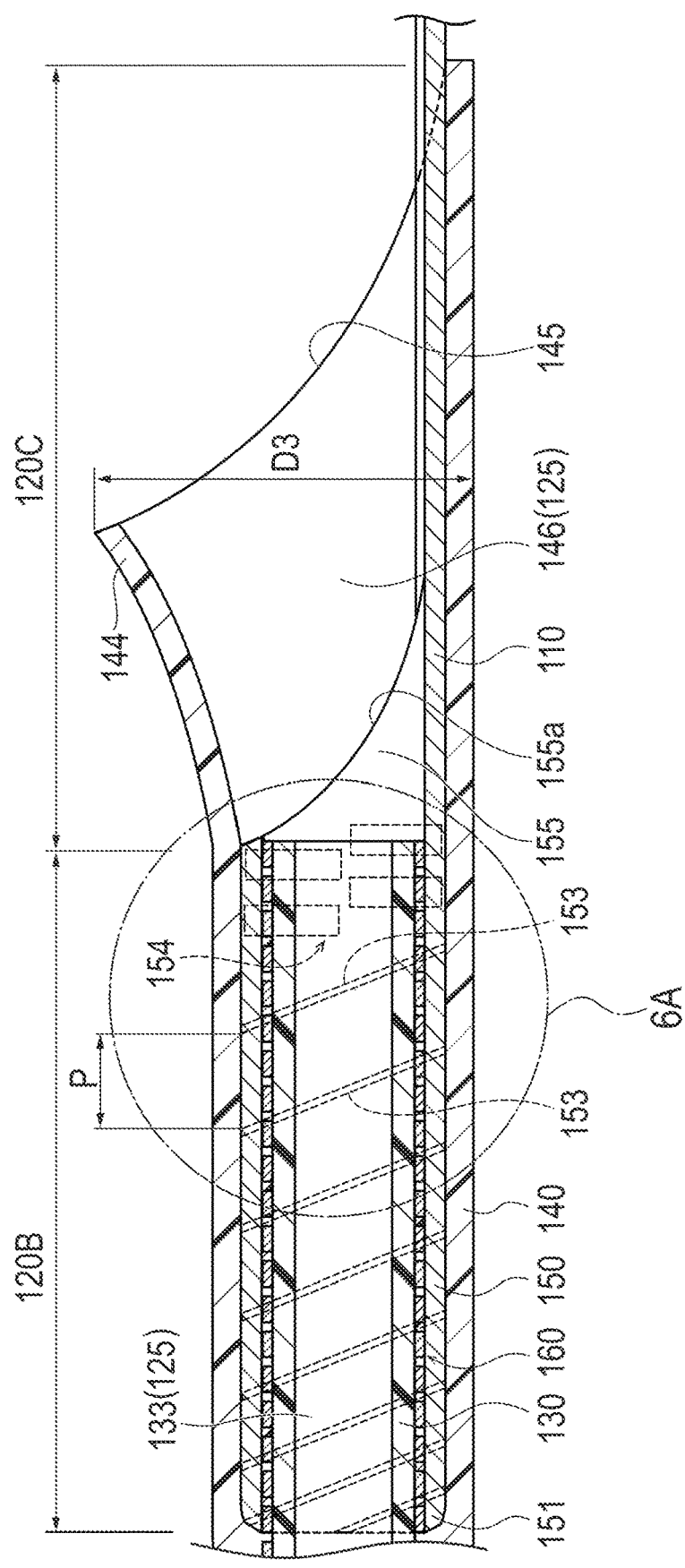
FIG. 4 is an enlarged cross-sectional view illustrating a second region and a third region of the distal member of the medical elongated body.

As illustrated in FIGS. 4 and 7B, the tubular member 150 has a hollow tubular structure. In the third region 120C formed closer to the proximal side than the second region 120B, the tubular member 150 has an inclined region 155 inclined toward the shaft portion 110. A proximal opening portion 155a opening to the proximal side is formed in the inclined region 155.

In accordance with an exemplary embodiment, as illustrated in FIG. 4, the tubular member 150 is connected to and integrated with the shaft portion 110, in a region closer to the proximal side than the inclined region 155.

Figure 7C:
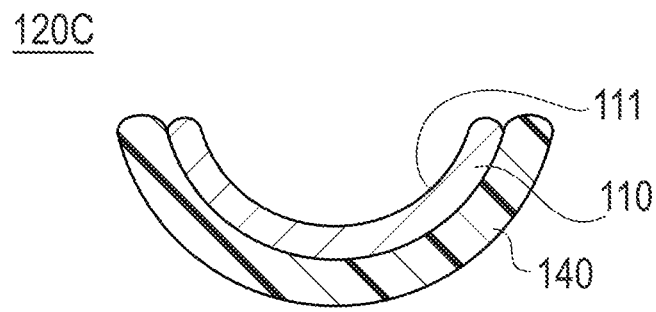
FIG. 7C is an axially orthogonal cross-sectional view of the third region of the distal member taken along an arrow-head line 7C-7C of FIG. 3.

As illustrated in FIGS. 4 and 7C, the distal side of the shaft portion 110 is formed into substantially a semicircular arc shape which is the shape of an axially orthogonal cross section. In accordance with an exemplary embodiment, an inner surface 111 of the shaft portion 110 has a concavely curved cross-sectional shape. Since the shaft portion 110 is formed into substantially a semicircular arc shape as described above, when the shaft portion 110 is inserted into the catheter main body portion 210 of the catheter 200, the shaft portion 110 is capable of reducing a sliding resistance applied between the catheter main body portion 210 and the shaft portion 110.

As illustrated in FIG. 2, the shaft portion 110 extends in substantially a semicircular arc shape to the proximal side on which the grip portion 180 is disposed. The grip portion 180 is fixed to the proximal side of the shaft portion 110.

As illustrated in FIGS. 3, 7A and 7B, the distal member 120 has a reinforcement layer 160 containing a metallic material and formed between the inner layer 130 and the outer layer 140 from the first region 120A to the second region 120B.

As illustrated in FIG. 7B, the reinforcement layer 160 is disposed inside the tubular member 150 in the second region 120B of the distal member 120.

Figure 6:
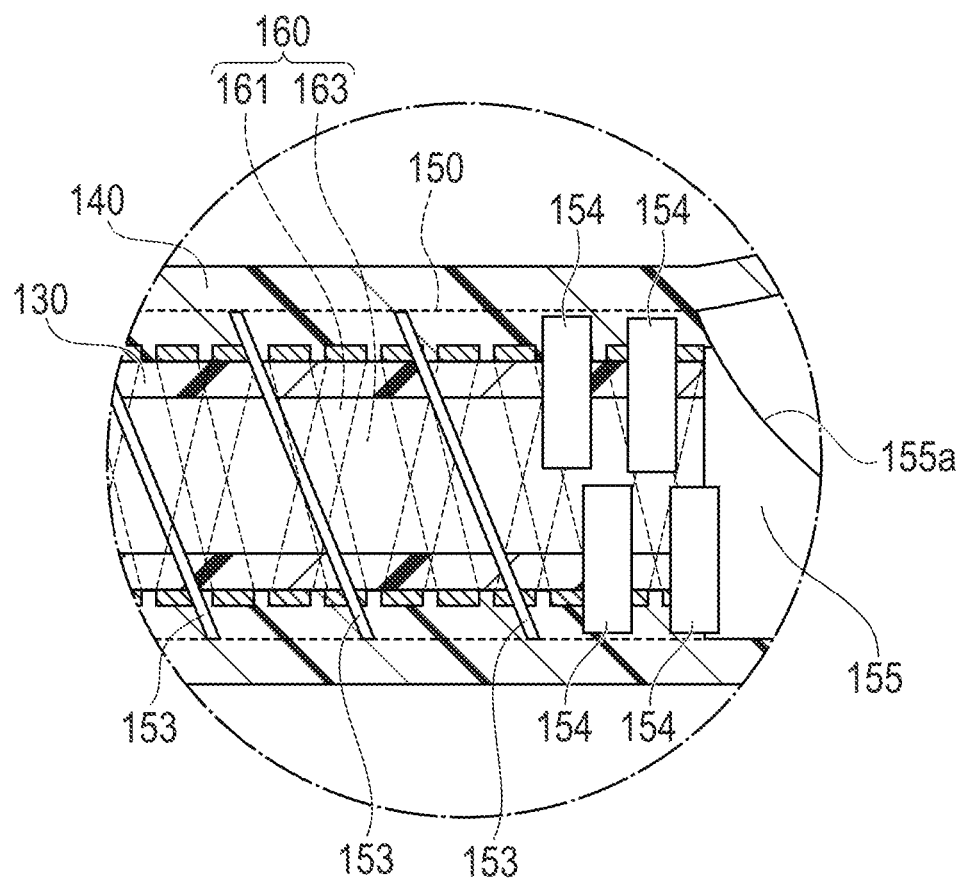
FIG. 6 is an enlarged view illustrating a portion surrounded by a broken line 6A of FIG. 4.

As illustrated in FIG. 6, the reinforcement layer 160 has a reinforcement member 161 formed of a metallic material, and a gap portion 163 formed in the reinforcement member 161.

In accordance with an exemplary embodiment, the gap portion 163 of the reinforcement member 161 connects together the inner layer 130 and the outer layer 140 in a state where the gap portion 163 is disposed between the inner layer 130 and the outer layer 140. Note that the connection implies a state where the inner layer 130 and the outer layer 140 are in physical contact with each other or a state where the inner layer 130 and the outer layer 140 can be, for example, melted and solidified together.

In accordance with an exemplary embodiment, the reinforcement member 161 of the reinforcement layer 160 is formed of a metallic material. The reinforcement layer 160 has a tubular structure formed by braiding a wire rod formed of a metallic material. A braided wire-rod portion forms the reinforcement members 161, and a mesh portion shaped by the reinforcement members 161 forms the gap portions 163.

The cross-sectional shape of the reinforcement member 161 is not specifically limited, and can be, for example, a rectangular or circular shape. In addition, for example, a one over and one under pattern in which the reinforcement members 161 intersect each other can be adopted as a braid pattern of the reinforcement member 161.

Note that the reinforcement layer 160 may be formed as, for example, a coil helically shaped along an axial direction.

As illustrated in FIG. 4, the tubular member 150 has a slit portion 153.

As illustrated in FIGS. 4 and 7B, in the second region 120B, the outer layer 140 can be welded to the inner layer 130 via each gap formed by the gap portion 163 of the reinforcement layer 160 and the slit portion 153 of the tubular member 150.

In order to help enable the inner layer 130 and the outer layer 140 to be welded together via both of the gap portion 163 and the slit portion 153, at least parts of both can be disposed to overlap each other in the axial direction and a circumferential direction. In accordance with an exemplary embodiment, the foregoing gap is formed in a region where the gap portion 163 and the slit portion 153 overlap each other in the axial direction and the circumferential direction.

As illustrated in FIG. 4, the slit portion 153 of the tubular member 150 is helically formed in the tubular member 150. In addition, a pitch P (axial distance between the slit portions 153 adjacent to each other) between the slit portions 153 can be such that the pitch P decreases from a proximal end toward a distal end of the tubular member 150.

As illustrated in FIG. 6, the tubular member 150 has a plurality of opening portions 154 in a region closer to a proximal side than a region where the slit portion 153 is formed. Therefore, the outer layer 140 can be reliably welded to the inner layer 130 via the opening portions 154, in a proximal portion of the tubular member 150 which is likely to come into contact with the medical device inserted into the distal member 120. Note that each of the slit portion 153 and the opening portion 154 is a hole (space) which is actually a non-existing member, but in FIG. 6, in order to clearly illustrate a positional relationship between both, the slit portion 153 and the opening portion 154 are illustrated in white.

The opening portion 154 is a hole that passes through the tubular member 150 in the wall thickness direction. A specific shape or the number of the opening portions 154 is not specifically limited.

Note that if the pitch P of the slit portion 153 of the tubular member 150 is such that the pitch P decreases from the proximal end toward the distal end of the tubular member 150, since the tubular member 150 has a small number of the slit portions 153 on the proximal side of the tubular member 150, it can be difficult for the gap portion 163 of the reinforcement layer 160 and the slit portion 153 of the tubular member 150 to form a gap, and it can be difficult to weld together the inner layer 130 and the outer layer 140. In this case, since the tubular member 150 has the opening portion 154 provided closer to the proximal side than the region where the slit portion 153 is formed, the inner layer 130 and the outer layer 140 can be suitably welded together.

As illustrated in FIG. 5, a distal portion 151 of the tubular member 150 can be formed into a tapered shape, the outer diameter of which decreases to the proximal side. Note that the shape of an end surface of the distal portion 151 of the tubular member 150 is not limited to a shape (rounded shape) which is curved (i.e., gently curved) to the distal side as illustrated, and for example, a distal surface may have a straight line shape which perpendicularly intersects the axial direction.

In addition, the tubular member 150 may have a shape in which the inner diameter and the outer diameter of the tubular member 150 decreases to the distal side in a stepwise manner or decreases continuously. It is possible to form the tubular member 150 with the foregoing shape, for example, the shape is formed by fixing the tubular member 150 to the reinforcement layer 160 with a swage process in a state where the reinforcement layer 160 is covered with the tubular member 150.

As illustrated in FIG. 4, the third region 120C of the distal member 120 is formed with a proximal opening portion 145 which is formed of a material more flexible than the material of the tubular member 150 and has an outer diameter increasing from a distal side toward a proximal side of the inclined region 155 of the tubular member 150.

The proximal opening portion 145 formed in the third region 120C is formed on a proximal side of the outer layer 140. In accordance with an exemplary embodiment, the lumen 146 of the proximal portion 144 of the outer layer 140 has a shape which becomes gradually wider (i.e., larger) to the proximal side, and the proximal opening portion 145 is formed at a proximal end of the lumen 146.

As illustrated in FIG. 4, the tubular member 150 has a cylindrical tubular structure in the vicinity of a distal end of the inclined region 155 of the tubular member 150. In a cylindrical portion of the tubular member 150, the tubular member 150 and the reinforcement layer 160 disposed inside the tubular member 150 overlap each other in the circumferential direction. In accordance with an exemplary embodiment, the shape of the tubular member 150 can be gradually transformed from the cylindrical shape to the shape (semicircular arc shape) of the shaft portion 110 from the distal side to the proximal side of the inclined region 155.

In accordance with an exemplary embodiment, a maximum diameter D3 of the proximal opening portion 145 formed in the third region 120C can be, for example, substantially equal to or greater than an inner diameter (diameter of the lumen 211) d1 (refer to FIG. 9) of the catheter main body portion 210 of the catheter 200. Note that the range of substantially the same dimension, for example, can contain a dimensional difference induced by manufacturing tolerances.

In accordance with an exemplary embodiment, if the inner diameter d1 of the catheter main body portion 210 of the catheter 200, for example, is from 1.4 mm to 2.2 mm, the maximum diameter D3 of the proximal opening portion 145, for example, is preferably from 1.4 mm to 2.2 mm, and more preferably from 1.7 mm to 1.9 mm.

If it is possible to cause the medical elongated body 100 to protrude from the catheter main body portion 210 by a desired length when using the medical elongated body 100 along with the catheter 200, the length of a portion of the medical elongated body 100 along the axial direction, which contains the distal member 120 and the shaft portion 110, is not specifically limited, and can be, for example, from 800 mm to 1,300 mm. In addition, the length of the distal member 120 along the axial direction can be, for example, from 100 mm to 300 mm. In addition, the length of the second region 120B of the distal member 120 along the axial direction can be, for example, from 10 mm to 100 mm. In addition, the length of the third region 120C of the distal member 120 along the axial direction can be, for example, from 5 mm to 50 mm.

Subsequently, a configuration material of the medical elongated body 100 will be described.

In accordance with an exemplary embodiment, the inner layer 130 and the outer layer 140 of the distal member 120 are each preferably made of a resin material more flexible than the material of the tubular member 150. The inner layer 130 and the outer layer 140 can be made of, for example, a polyolefin such as polyethylene, polypropylene, an ethylene-propylene copolymer, or an ethylene-vinyl acetate copolymer, a thermoplastic resin such as soft polyvinyl chloride, any of various elastomers such as polyurethane elastomer, polyamide elastomer, or polyester elastomer, fluorine resin such as polytetrafluoroethylene, polyamide, or a crystalline plastic such as crystalline polyethylene or crystalline polypropylene.

The distal tip 170 can be made from, for example, a polymer material such as polyolefin (for example, polyethylene, polypropylene, polybutene, ethylene-propylene copolymer, ethylene-vinyl acetate copolymer, ionomer, or a mixture of two or more of the polymer materials), polyvinyl chloride, polyamide, polyamide elastomer, polyurethane, polyurethane elastomer, polyimide, or fluorine resin, any mixture of the polymer materials, or a multilayer tubular member made of two or more of the polymer materials. Note that the distal tip 170 is preferably made from a material more flexible than the materials of the inner layer 130 and the outer layer 140.

In accordance with an exemplary embodiment, the shaft portion 110 and the tubular member 150 can be made from a metallic material, such as stainless steel or super-elastic alloy such as Ni—Ti-based alloy, Ni—Al-based alloy, or Cu—Zn-based alloy.

For example, the reinforcement member 161 of the reinforcement layer 160 can be made from the same materials as the exemplary materials of the shaft portion 110 and the tubular member 150.

Subsequently, a use example of the medical instrument set 10 (the medical elongated body 100 and the catheter 200) will be described.

For example, when performing a procedure on a lesion area N such as stenosed site formed in a coronary artery by using a medical device (not illustrated) such as balloon catheter or stent delivery device, an operator or the like disposes a distal end of the catheter 200 in the vicinity of an entrance of the coronary artery so that the medical device inserted into the catheter 200 can be supported when being delivered to the lesion area. However, if the lesion area N such as stenosed site is spaced apart from the vicinity of the entrance of the coronary artery, even though the distal end of the catheter 200 is disposed in the vicinity of the entrance of the coronary artery, the medical device may not receive a sufficient support force when being inserted into the catheter 200. In this case, the operator inserts the catheter 200 further inside (to the lesion area N) of the coronary artery, and attempts to deliver the medical device to the lesion area N in a state where the medical device has received greater support force.

Figure 8:
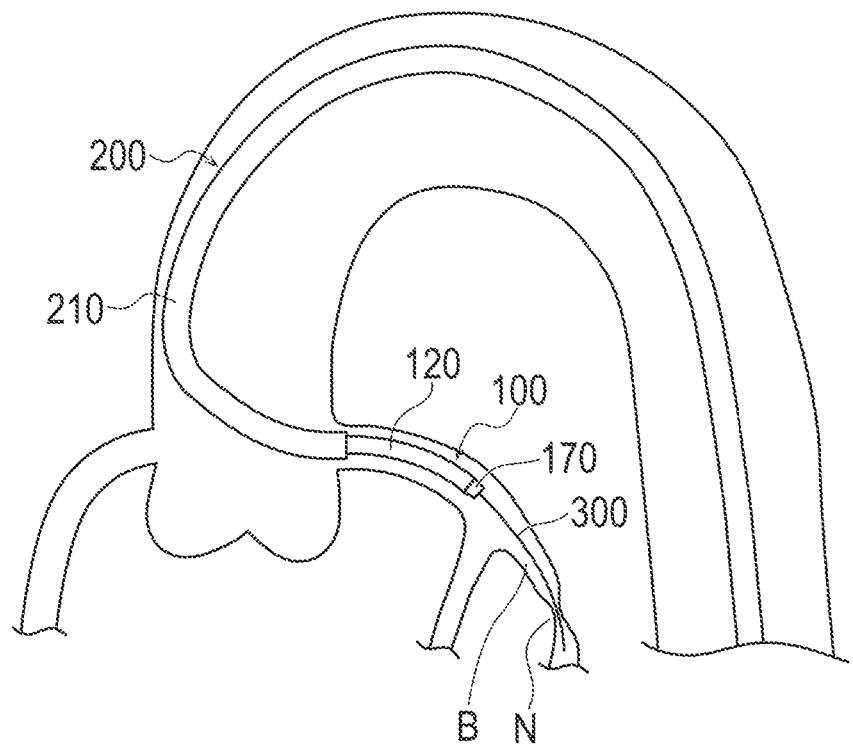
FIG. 8 is a schematic view illustrating a use example of the medical instrument set according to the embodiment.

At that time, if the catheter 200 has a relatively large diameter, the catheter 200 has a potential for causing ischemia or the like. For this reason, as illustrated in FIG. 8, the operator delivers the medical elongated body 100, which is thinner, to a distal side of the catheter 200 via the catheter 200. Specifically, if the lesion area N such as stenosed site is spaced apart from the vicinity of the entrance of the coronary artery, before inserting the medical device or after extracting the medical device from the catheter 200 for the moment, the operator inserts the medical elongated body 100.

Figure 9:
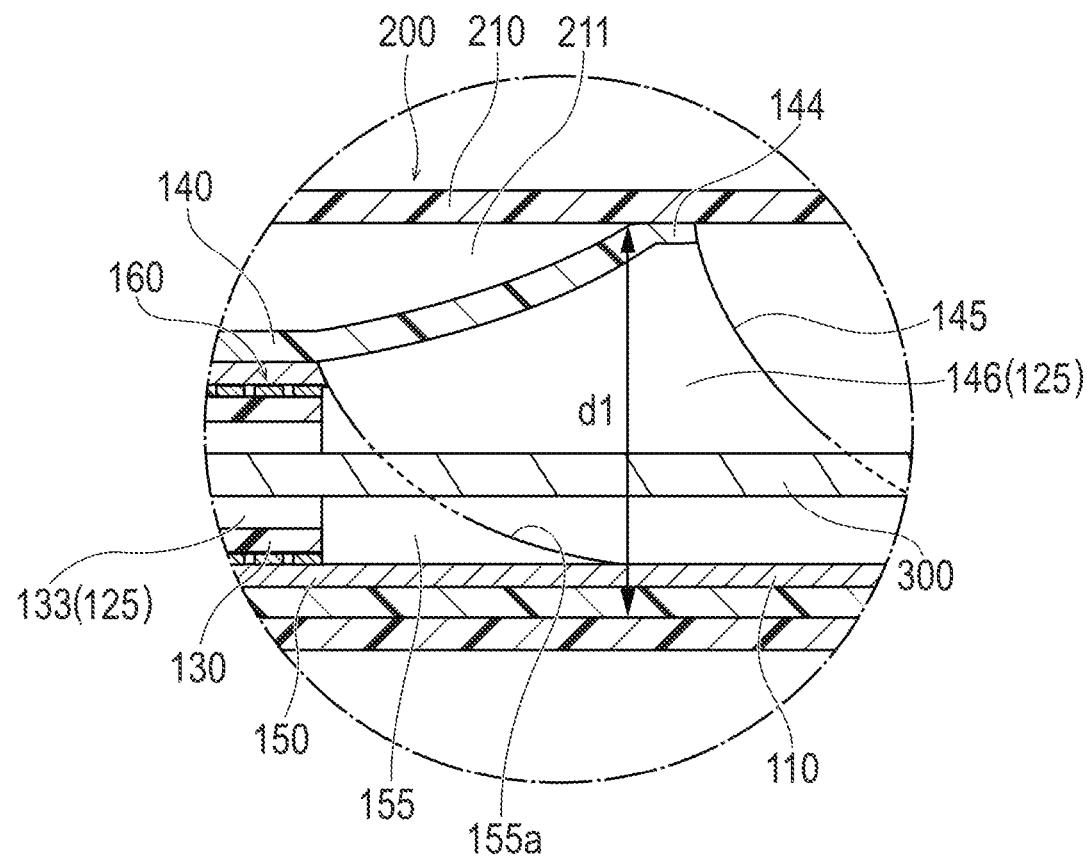
FIG. 9 is an enlarged cross-sectional view for describing effects of the medical instrument set according to the embodiment.

As illustrated in FIG. 9, when delivering the medical device, the operator delivers the medical elongated body 100 to a desired position along a guide wire 300 inserted into the catheter 200. The operator can cause the distal side of the distal member 120 of the medical elongated body 100 to protrude from the catheter 200 by a predetermined length, and delivers the medical device via the medical elongated body 100 in a state where the medical device has received a desired support force.

When the medical elongated body 100 is delivered via the catheter 200, as illustrated in FIG. 9, the proximal portion 144 of the outer layer 140 is brought into contact with an inner surface of the catheter main body portion 210 of the catheter 200. At that time, the proximal portion 144 of the outer layer 140 can be flexibly deformed along the inner surface of the catheter main body portion 210, and a clearance between the inner surface of the catheter main body portion 210 and the proximal portion 144 decreases. Therefore, the operator can be capable of rather smoothly moving the medical elongated body 100 along the catheter 200. In addition, the operator can prevent the medical device, which is inserted into the lumen 125 of the distal member 120 from the proximal opening portion 145 of the outer layer 140, from being caught in the clearance by decreasing the clearance between the proximal portion 144 of the outer layer 140 and the inner surface of the catheter main body portion 210. Therefore, the operator can rather smoothly insert the medical device into the lumen 125 of the distal member 120.

Furthermore, when supplying the contrast agent from the side branch 223 of the catheter 200, the operator can help prevent an occurrence of an event such as the contrast agent flowing into the clearance between the proximal portion 144 of the outer layer 140 and the inner surface of the catheter main body portion 210 and being charged in full from the distal opening portion 211a of the catheter main body portion 210 (refer to FIG. 1). For example, the operator can cause the contrast agent to be sent to the distal side of the medical elongated body 100 which has protruded to the distal side of the catheter 200, and the contrast agent to be discharged to the lesion area which is a treatment target, and an area in the periphery of the lesion area. Therefore, the operator can acquire a desired contrast image.

Subsequently, effects of the medical elongated body 100 and the medical instrument set 10 according to the embodiment will be described.

The medical elongated body 100 according to the present disclosure has the shaft portion 110 made of a linear body, and the distal member 120 which is formed on the distal side of the shaft portion 110 and has the lumen 125. The distal member 120 has the first region 120A having the inner layer 130 and the outer layer 140 which are made of a resin material, and the second region 120B having the inner layer 130, the outer layer 140, and the tubular member 150 which is made of a metallic material and is disposed between the inner layer 130 and the outer layer 140. The tubular member 150 forming the second region 120B is integrally formed with the shaft portion 110. The distal member 120 has the reinforcement layer 160 containing a metallic material and formed between the inner layer 130 and the outer layer 140 from the first region 120A to the second region 120B. Furthermore, the reinforcement layer 160 is disposed inside the tubular member 150 in the second region 120B. The outer diameter of the first region 120A is set smaller than the outer diameter of the second region 1206.

In the medical elongated body 100 with the foregoing configuration, the shaft portion 110 made of a linear body can be integrally formed with the tubular member 150 forming the second region 120B of the distal member 120. For this reason, in the medical elongated body 100, a physical property difference in a boundary portion (physical property change region) between the shaft portion 110 and the tubular member 150 can be kept relatively small, and an occurrence of a kink can be prevented.

In addition, the medical elongated body 100 with the foregoing configuration is capable of improving the contrast property of the second region 1206 by virtue of the tubular member 150 forming the second region 120B, and the reinforcement layer 160 containing a metallic material and disposed inside the tubular member 150 in the second region 120B. For this reason, it is not necessary to separately provide a contrast marker (contrast ring) for indicating the vicinity of a proximal portion of the second region 120B, and thus the medical elongated body 100 with the configuration as disclosed is capable of improving the contrast property of the second region 1208, and preventing an occurrence of a physical property difference which results from the placement of the contrast marker.

In addition, since the outer diameter of the first region 120A of the distal member 120 is smaller than the outer diameter of the second region 120B, the ease to insert the medical elongated body 100 with the foregoing configuration into a body lumen can be improved.

In accordance with an exemplary embodiment, the outer layer 140 of the distal member 120 according to the embodiment has the inclined portion 143, the outer diameter of which decreases from the distal end of the second region 120B toward the distal side. For this reason, it is possible to prevent a deterioration in the ease to insert the medical elongated body 100 which is caused due to the second region 120B being caught by the catheter 200, the body lumen, or the like. Therefore, when inserting the medical elongated body 100 into the body lumen, an operator can smoothly insert the first region 120A and consecutively the second region 120B into the body lumen.

In addition, in the medical elongated body 100 according to the embodiment, in the axially orthogonal cross section of the distal member 120, the wall thickness t1 of the outer layer 140 in the first region 120A closer to the distal side than the inclined portion 143 is substantially the same as the wall thickness of the outer layer 140 in the second region 120B. For this reason, the physical property difference in the boundary portion between the first region 120A and the second region 120B can be kept relatively small, and an occurrence of a kink can be prevented.

In addition, the reinforcement layer 160 according to the embodiment has the reinforcement member 161 formed of a metallic material, and the gap portion 163 which is formed in the reinforcement member 161 and connects together the inner layer 130 and the outer layer 140. In addition, the tubular member 150 has the slit portion 153. In addition, in the second region 120B, the outer layer 140 is welded to the inner layer 130 via each gap formed by the gap portion 163 of the reinforcement layer 160 and the slit portion 153 of the tubular member 150. For this reason, in the medical elongated body 100, it is possible to suitably weld together the inner layer 130 and the outer layer 140 which are disposed such that the reinforcement member 161 formed of a metallic material and the tubular member 150 formed of a metallic material can be interposed (i.e., placed) between inner layer 130 and the outer layer 140.

In addition, the slit portion 153 of the tubular member 150 according to the embodiment is helically formed in the tubular member 150. The pitch of the slit portion 153 decreases from the proximal end toward the distal end of the tubular member 150. For this reason, in the medical elongated body 100, the flexibility of a distal side (the distal side of the tubular member 150) of the second region 120B improves, and thus the ease to insert the second region 120B into the body lumen improves. Furthermore, since the tubular member 150 has the plurality of opening portions 154 in the region closer to the proximal side than the region where the slit portion 153 is formed in the tubular member 150, it is possible to suitably weld together the inner layer 130 and the outer layer 140 on the proximal side of the tubular member 150 via the opening portions 154.

In addition, the distal member 120 according to the embodiment has the third region 120C closer to the proximal side than the second region 120B. In the third region 120C, the tubular member 150 has the inclined region 155 inclined toward the shaft portion 110. The third region 120C is formed with the proximal opening portion 145 which is formed of a material more flexible than the material of the tubular member 150, and the outer diameter of which increases from the distal side toward the proximal side of the inclined region 155. For this reason, when the medical elongated body 100 is inserted into the catheter main body portion 210 of the catheter 200, it is possible to decrease the clearance between the medical elongated body 100 and the catheter main body portion 210, and a movement of the medical elongated body 100 with respect to the catheter 200 becomes relatively smooth. Furthermore, the medical elongated body 100 is capable of improving the ease of inserting the medical device into the lumen 125 of the medical elongated body 100, and discharging the contrast agent to a proper position inside the body lumen.

In addition, the medical instrument set 10 according to the embodiment can include the medical elongated body 100, and the catheter 200 having the catheter main body portion 210 formed with the lumen 211 into which the medical elongated body 100 can be inserted. In accordance with an exemplary embodiment, the maximum outer diameter of the proximal opening portion 145 of the medical elongated body 100 can be equal to or greater than the inner diameter of the catheter main body portion 210. For this reason, in a procedure using the medical elongated body 100 and the catheter 200, the medical instrument set 10 can smoothly deliver the medical elongated body 100 and the medical device to a desired position inside the body lumen, and properly discharging the contrast agent to the desired position inside the body lumen.

The medical elongated body according to the present disclosure has been described with reference to the embodiment, but the present disclosure is not limited only to the configuration described in the embodiment, and can be appropriately changed based on description of the claims.

For example, the distal member of the medical elongated body may have at least the first region and the second region, and may not have the third region.

In addition, the cross-sectional shape of the shaft portion of the medical elongated body is not limited to the shape (semicircular arc shape) illustrated, and can be appropriately changed.

In addition, the catheter described in the embodiment is merely an example, and if the medical elongated body can be inserted into and delivered by the catheter, the configuration of the catheter is not specifically limited.

In addition, each configuration part of the medical elongated body can be replaced with a desired part capable of exhibiting the same function. In addition, a desired component (member) which has not been specifically described in the specification may appropriately be added to the medical elongated body.

The detailed description above describes to a medical elongated body and a medical instrument set. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A medical elongated body comprising:
a shaft portion made of a linear body;
a distal member formed on a distal side of the shaft portion and having a lumen, the distal member having a first region having an inner layer and an outer layer which are made of a resin material, and a second region having the inner layer, the outer layer, and a tubular member made of a metallic material and disposed between the inner layer and the outer layer in the second region, the tubular member forming the second region being integrally formed with the shaft portion;
a reinforcement layer containing a metallic material arranged between the inner layer and the outer layer of the first region to the inner layer and the outer layer of the second region of the distal member, the reinforcement layer being disposed inside of the tubular member in the second region;
wherein the reinforcement layer has a reinforcement member formed of a metallic material, and a gap portion formed in the reinforcement member connecting the inner layer to the outer layer;

the tubular member having a slit portion, and wherein in the second region, the outer layer is welded to the inner layer via a gap formed by the gap portion of the reinforcement layer and the slit portion of the tubular member; and wherein an outer diameter of the first region is smaller than an outer diameter of the second region.

2. The medical elongated body according to claim 1, wherein the outer layer of the distal member has an inclined portion having an outer diameter decreasing from a distal end of the second region toward a distal side of the distal member.

3. The medical elongated body according to claim 2, wherein in an axially orthogonal cross section of the distal member, a wall thickness of the outer layer in the first region closer to the distal side than the inclined portion is the same as a wall thickness of the outer layer in the second region.

4. The medical elongated body according to claim 1, wherein the slit portion is helically formed in the tubular member, and a pitch of the slit portion decreases from a proximal end toward a distal end of the tubular member.

5. The medical elongated body according to claim 4, wherein the tubular member has a plurality of opening portions in a region closer to a proximal side than a region where the slit portion is formed.

6. The medical elongated body according to claim 1, wherein the distal member has a third region, the third region being closer to a proximal side of the distal member than the second region.

7. The medical elongated body according to claim 6, wherein the tubular member has an inclined region inclined toward the shaft portion in the third region, and the third region includes a proximal opening portion and the third region has an outer diameter increasing from a distal side toward a proximal side of the inclined region.

8. The medical elongated body according to claim 7, wherein a material of the third region is more flexible than a material of the tubular member.

9. A medical instrument set comprising:
the medical elongated body according to claim 7; and
a catheter having a catheter main body portion with a lumen into which the medical elongated body is insertable, and wherein a maximum outer diameter of the proximal opening portion of the medical elongated body is equal to or greater than an inner diameter of the catheter main body portion.

10. A treatment method for performing a procedure on a lesion inside a biological lumen using the medical elongated body according to claim 1, the method comprising:
inserting a guide wire into the biological lumen;
inserting a catheter into the biological lumen along the guide wire;
delivering the medical elongated body to a position distally of a distal end of the catheter via the catheter and along the guide wire; and
delivering a medical device via the medical elongated body in a state where the medical device has received a desired support force.

11. A medical elongated body comprising:
a shaft portion;
a distal member formed on a distal side of the shaft portion and having a lumen, the distal member having a first region, a second region, and a third region, the first region having an inner layer and an outer layer, the second region having the inner layer, the outer layer, and a tubular member, the tubular member being disposed between the inner layer and the outer layer in the second region, and an outer diameter of the first region being smaller than an outer diameter of the second region;
a reinforcement layer containing a metallic material arranged between the inner layer and the outer layer of the first region to the inner layer and the outer layer of the second region of the distal member, the reinforcement layer being disposed inside of the tubular member in the second region;
the tubular member having an inclined region inclined toward the shaft portion in the third region, the third region including a proximal opening portion and the third region has an outer diameter increasing from a distal side toward a proximal side of the inclined region;
wherein the reinforcement layer has a reinforcement member formed of a metallic material, and a gap portion formed in the reinforcement member connecting the inner layer to the outer layer; and
the tubular member having a slit portion, and wherein in the second region, the outer layer is welded to the inner layer via a gap formed by the gap portion of the reinforcement layer and the slit portion of the tubular member.

12. The medical elongated body according to claim 11, wherein the outer layer of the distal member has an inclined portion having an outer diameter decreasing from a distal end of the second region toward a distal side of the distal member; and
wherein in an axially orthogonal cross section of the distal member, a wall thickness of the outer layer in the first region closer to the distal side than the inclined portion is the same as a wall thickness of the outer layer in the second region.

13. The medical elongated body according to claim 11, wherein the slit portion is helically formed in the tubular member, and a pitch of the slit portion decreases from a proximal end toward a distal end of the tubular member, and wherein the tubular member has a plurality of opening portions in a region closer to a proximal side than a region where the slit portion is formed.

14. A medical instrument set comprising:
the medical elongated body according to claim 11; and
a catheter having a catheter main body portion with a lumen into which the medical elongated body is insertable, and wherein a maximum outer diameter of the proximal opening portion of the medical elongated body is equal to or greater than an inner diameter of the catheter main body portion.

15. A medical instrument set comprising:
a medical elongated body which includes a shaft portion made of a linear body, a distal member formed on a distal side of the shaft portion and having a lumen, the distal member having a first region having an inner layer and an outer layer which are made of a resin material, and a second region having the inner layer, the outer layer, and a tubular member made of a metallic material and disposed between the inner layer and the outer layer in the second region, the tubular member forming the second region being integrally formed with the shaft portion, a reinforcement layer containing a metallic material arranged between the inner layer and the outer layer of the first region to the inner layer and the outer layer of the second region of the distal member, the reinforcement layer being disposed inside of the tubular member in the second region, and wherein an outer diameter of the first region is smaller than an outer diameter of the second region, the reinforcement layer having a reinforcement member formed of a metallic material, and a dap portion formed in the reinforcement member connecting the inner layer to the outer layer, the tubular member having a slit portion, and wherein in the second region, the outer layer is welded to the inner layer via a dap formed by the gap portion of the reinforcement layer and the slit portion of the tubular member; and a catheter having a catheter main body portion with a lumen into which the medical elongated body is insertable, and wherein a maximum outer diameter of the proximal opening portion of the medical elongated body is equal to or greater than an inner diameter of the catheter main body portion.

16. The medical elongated body according to claim 15, wherein the outer layer of the distal member has an inclined portion having an outer diameter decreasing from a distal end of the second region toward a distal side of the distal member, and wherein in an axially orthogonal cross section of the distal member, a wall thickness of the outer layer in the first region closer to the distal side than the inclined portion is the same as a wall thickness of the outer layer in the second region.

* * * * *